United States Patent [19]

Pinke

[11] 3,959,386

[45] May 25, 1976

[54] PRODUCTION OF PRIMARY COMPOUNDS

[75] Inventor: Paul A. Pinke, Des Plaines, Ill.

[73] Assignee: Universal Oil Products Company, Des Plaines, Ill.

[22] Filed: May 13, 1974

[21] Appl. No.: 469,162

[52] U.S. Cl. .................. 260/604 HF; 260/632 HF; 252/472
[51] Int. Cl.² ........................................ C07C 27/22
[58] Field of Search ............... 260/604 HF, 632 HF

[56] References Cited
UNITED STATES PATENTS

| | | | |
|---|---|---|---|
| 3,351,666 | 11/1967 | Kern et al. ..................... | 260/604 HF |
| 3,511,880 | 5/1970 | Booth ........................... | 260/604 HF |
| 3,644,445 | 2/1972 | Kroll ............................. | 260/604 HF |

*Primary Examiner*—Bernard Helfin
*Assistant Examiner*—James H. Reamer
*Attorney, Agent, or Firm*—James R. Hoatson, Jr.; Raymond H. Nelson; William H. Page, II

[57] ABSTRACT

A process which comprises treating unsaturated compounds with an aluminum-containing compound and an aluminum metal in an atmosphere of hydrogen and subsequently contacting the treated compounds with carbon monoxide and hydrogen in the presence of a catalyst comprising a compound containing a metal selected from Group VIII of the Periodic Table and recovering the resultant primary compounds.

8 Claims, No Drawings

PRODUCTION OF PRIMARY COMPOUNDS

This invention relates to a process for the production of primary compounds. More specifically, this invention relates to a process for the preparation of primary compounds which comprises treating unsaturated compounds with an aluminum-containing compound and an aluminum metal in an atmosphere comprising hydrogen and subsequently contacting the treated compounds with carbon monoxide and hydrogen in the presence of a catalyst comprising a compound containing a metal selected from Group VIII of the Periodic Table.

Processes directed to the production of reaction mixtures comprising substantial amounts of aldehydes and alcohols by various reactions of unsaturated compounds with carbon monoxide and hydrogen in the presence of certain catalysts are well-known in the art. The aldehydes and alcohols produced generally correspond to the compounds obtained by the addition of a carbonyl to an olefinically unsaturated carbon atom in the starting material with simultaneous saturation of the olefinic bond. Furthermore, saturation of the aldehyde compound with hydrogen will afford the corresponding alcohol. One such process is known as hydroformylation and involves a reaction which may be shown by the generic formula $$R_1-\overset{R_2}{\underset{R_3}{C}} = C-R_4 + CO + H_2 \xrightarrow[\Delta]{\text{Catalyst}} R_1-\overset{R_2}{\underset{H}{C}}-\overset{R_3H}{\underset{R_4}{C}}-C = o \text{ and/or } R_1-\overset{R_2}{\underset{H}{C}}-\overset{R_3}{\underset{R_4H}{C}}-\overset{OH}{\underset{}{C}}-H$$

FORMULA I where $R_1$, $R_2$, $R_3$, or $R_4$ may be chosen from a group comprising an organic radical, a halide or a hydrogen radical.

It has been shown in the prior art that dicobalt octacarbonyl has generally been used as a catalyst for the hydroformylation of these unsaturated compounds. This catalyst which can be prepared from many forms of cobalt, usually decomposes rapidly unless high pressures of about 200–4500 pounds per square inch guage of carbon monoxide are maintained. Correspondingly, for this reaction, high pressures of hydrogen are also necessary. A basic serious disadvantage of the hydroformylation or "oxo" processes has been the inability to produce terminal aldehydes and/or alcohols from a mixture of unsaturated compounds in which both internal and terminal olefins are present, further, the hydroformylation of terminal olefins does not give completely terminal aldehydes and/or alcohols but rather, at best, a 80–90% terminal product. In contradistinction to the prior art, it has now been shown that primary compounds can be prepared from the treatment of unsaturated compounds comprising both internal and terminal unsaturated compounds by treatment with an aluminum-containing compound and an aluminum metal in an atmosphere comprising hydrogen and subsequently contacting the treated compound with carbon monoxide and hydrogen in the presence of a catalyst comprising a compound containing a metal selected from Group VIII of the Periodic Table. The utilization of the present invention will allow the manufacturer to have a greater source of primary products from a greater variety of charge stocks while reducing his burden for the separation and disposal of the undesirable internal or "branched" products.

The desired products to the process of this invention, namely alcohols and aldehydes, are utilized in the chemical industry in many ways. For example, primary alcohols and/or aldehydes are utilized as solvents, as an extraction medium, in the synthesis of other organic derivatives, synthetic drugs, as dyes, in synthetic rubber, in detergents, as cleaning solutions, in surface coatings, as cosmetics, in pharmaceuticals, in the preparation of esters, as a solvent for resin in coatings, as a plasticizer, as a dying assistant, in hydraulic fluids, in detergent formulations, as dehydrating agents, as perfumeries.

It is therefore an object of this invention to provide a process for the preparation of primary aldehydes and primary alcohols.

A further object of this invention is to provide an improvement in a process for the preparation of primary aldehydes and primary alcohols utilizing certain catalytic compositions of matter which will permit the recovery of the desired primary compounds from a more variable charge stock containing both internal and terminal unsaturated compounds in a more economically feasible manner.

In one aspect an embodiment of this invention resides in a process which comprises treating unsaturated compounds with an aluminum-containing compound and an aluminum metal in an atmosphere comprising hydrogen, subsequently contacting the treated compounds with carbon monoxide and hydrogen in the presence of a catalyst comprising a compound containing a metal selected from Group VIII of the Periodic Table at reaction conditions, and recovering the resultant primary compound.

A specific embodiment of this invention resides in a process for preparing linear alcohols which comprises the treatment of octene-3 with triethyl aluminum and aluminum metal in a hydrogen atmosphere of about 2000 to about 3500 psi and a temperature of from about 50°C to about 200°C to produce tri-n-octyl aluminum which is subsequently converted to linear alcohols by reacting said tri-n-octyl aluminum with hydrogen and carbon monoxide at a pressure of about 20 psi to about 4000 psi and a temperature of about 25°C to about 400°C in the presence of a catalyst comprising bis-(tributyl phosphine)nickel chloride.

Other objects and embodiments will be found in the following further detailed description of the present invention.

As hereinbefore set forth, the present invention is concerned with the process for preparing primary alcohols and primary aldehydes, said process being effected by contacting a mixture of both internal and terminal unsaturated compounds with an aluminum-containing compound and an aluminum metal in an atmosphere of hydrogen and subsequently contacting the treated compound with carbon monoxide and hydrogen in the presence of a catalyst comprising a compound containing a metal selected from Group VIII of the Periodic Table.

The unsaturated compound is treated with an aluminum-containing compound and aluminum metal at treatment conditions which include a temperature of from about 50°C to about 200°C and a pressure of 14 psi to about 4000 psi. When superatmospheric pressure is involved the pressure may be afforded by the presence of the hydrogen atmosphere or it is also contemplated that any other inert gas such as nitrogen may be present in conjunction with the hydrogen atmosphere. The reaction of the treated products with the hydrogen and carbon monoxide in the presence of a metal selected from Group VIII of the Periodic Table is effected at reaction conditions which include a temperature of from about 25°C to about 400°C and a pressure of from about 14 psi to about 4000 psi. When superatmosphere pressures are employed the pressure may be afforded by the introduction of carbon monoxide and hydrogen to the reaction zone or the pressure may be augmented by the presence of any substantially inert gas such as nitrogen or helium.

Examples of suitable mixtures of unsaturated compounds which are utilized as the starting material in the present invention would include, in particular, butene-1, butene-2, isobutene, pentene-1, pentene-2; 2-methylpentene-1, 2-methylpentene-2, heptene-3, 2-methylhexene-2, 3-methylhexene-2, octene-1, octene-2, octene-3, 3-methylheptene-1, 2-methylheptene-2; nonene-1, nonene-2, nonene-3, 3-methyloctene-2, decene-1, decene-2, decene-3, decene-4, decene-5, 3,4-dimethyloctene-2, 4-ethyloctene-2, undecene-1, undecene-2; decene-4, decene-5, decene-6, undecene-4, undecene-5, dodecene-4, dodecene-5, tridecene-6; dodecene-3, tridecene-2, tetradecene-3, pentadecene-5, tridecene-1, hexadecene-1, hexadecene-3, heptadecene-6, heptene-1, decene-1, decene-2, dodecene-5, tridecene-3, tetradecene-1, pentadecene-3, pentadecene-6, heptadecene-6; or mixtures of linear internal and terminal olefins such as the internal and terminal olefins possessing carbon numbers ranging from 11 to 14, 15 to 18 and 18 to 21.

It is understood that the aforementioned unsaturated compound mixtures are only representative of the class of compounds which may be employed as a starting material of the process of the present invention and that the invention is not necessarily limited thereto.

The catalytic compositions of matter which are utilized in the treatment of the unsaturated compounds comprise an aluminum-containing compound and an aluminum metal in the presence of an atmosphere comprising hydrogen. The aluminum-containing compound comprises a trialkyl aluminum or an alkyl aluminum hydride as exemplified, in particular, by trimethyl aluminum, triethyl aluminum, triisobutyl aluminum, dimethyl aluminum hydride, diethyl aluminum hydride, dipropyl aluminum hydride, diisopropyl aluminum hydride, dibutyl aluminum hydride, diisobutyl aluminum hydride, diamyl aluminum hydride, diisoamyl aluminum hydride, dihexyl aluminum hydride, diisohexyl aluminum hydride, di-t-hexyl aluminum hydride, diheptyl aluminum hydride, diisoheptyl aluminum hydride, di-t-heptyl aluminum hydride, dioctyl aluminum hydride, dinonyl aluminum hydride, didecyl aluminum hydride, diundecyl aluminum hydride, di-(2,3-dimethylpentyl)aluminum hydride, di-(2,3,4-triethylnonyl)aluminum hydride, di-(2,3-dimethylnonyl)aluminum hydride, etc. The catalytic compositions of matter which are utilized in the contacting of the product recovered from the treating procedure with carbon monoxide and hydrogen comprise a compound containing a metal selected from Group VIII of the Periodic Table. The metal may be selected from any of the following, namely, iron, cobalt, nickel, ruthenium, rhodium, palladium, osmium, iridium or platinum and may comprise such compounds as exemplified by bis-(tributyl phosphine) nickel chloride, triphenyl phosphine rhodium trichloride, tributyl phosphine cobalt chloride, tributyl phosphine ruthenium chloride, biscyclooctadienyl nickel, iron chloride, cobalt chloride, nickel dichloride, ruthenium trichloride, rhodium trichloride, palladium chloride, osmium chloride, iridium chloride, platinum chloride, nickel acetylacetonate, rhodium acetyl acetonate, palladium acetylacetonate, osmium acetylacetonate, iridium acetylactonate, nickel dicyclooctadiene-1,5, ruthenium dicyclooctadiene-1,5, rhodium dicyclooctadiene-1,5 irridium dicyclooctadiene-1,5, palladium dicyclooctadiene-1,5, platinum dicyclooctadiene-1,5, etc. The stability of the metal catalyst as well as the selectivity may be improved through the use of a stabilizing ligand based on either phosphorous, nitrogen, or arsenic. Some examples would include the trialkyl triaryl and mixed alkyl and aryl derivatives such as trimethyl, triethyl, tripropyl, tributyl, tricyclohexyl-, triphenyl-, dialkyl phenyl-, alkyl diphenyl-, phosphines, amines or arsines.

It is understood that the aforementioned compounds containing aluminum and compounds containing a metal selected from Group VIII of the Periodic Table are only representative of the catalytic compositions of matter and are not necesarily limited thereto.

It is contemplated in the scope of this invention that the process for obtaining the desired primary aldehydes and primary alcohols may be effected in a continuous manner of operation. When such a type of operation is employed the reactants comprising the unsaturated compound, both internal and terminal, are continuously charged to a treatment zone containing a catalyst comprising an alumina-containing compound and an aluminum metal, said treatment zone being equipped with a hydrogen feed system. The product of the treatment zone is charged to a reaction zone containing a catalyst comprisng a compound containing a metal selected from Group VIII of the Periodic Table, carbon monoxide and hydrogen entry devices. After completion of the desired residence time, the reactor effluent is continuously withdrawn from the reaction zone and subjected to conventional means of separation whereby the desired primary aldehydes or primary alcohols are recovered while any effective amount of carbon monoxide, hydrogen, Group VIII metal compound, aluminum-containing compound or aluminum metal is recycled to the reaction zone to the requisite reactor placement for attainment of the respective functions.

Examples of primary aldehydes and primary alcohols which may be prepared according to the process of this invention will include butanol, pentanol, hexanol, heptanol, octanol, nonanol, decanol, 2-methylbutanol-1, 2-methylpentanol-1, 2-ethylpentanol-1, 2-methylhexanol-1, 2-ethylhexanol-1, 2-ethyl-butanal, pentanal, hexanal, heptanal, octanal, nonanal, decanal, undecanal, dodecanl, tridecanal, tetradecanal, pentadecanal, 2-methylbutanal, 2-methyloctanal, 2-ethylhexanal.

The following examples are given to illustrate the process of the present invention which, however, are not intended to limit the generally broad scope of the present invention in strict accordance therewith.

EXAMPLE I

In this example 11.2 grams(0.1 mol) of octene-3, 0.2 grams of triethyl aluminum and 1.0 grams of aluminum are charged to a rotating autoclave equipped with heating and hydrogen entry devices. The autoclave is heated to a temperature of 150°C and charged with hydrogen gas to effect a pressure of 1000 psi, said physical conditions of pressure and temperature maintained at constant values for a period of time comprising 3 hours. At the end of the 3 hour period of time the autoclave is vented thereby allowing it to return to ambient pressure and the heat terminated thereby allowing it to return to room temperature at which point in time the treatment product is removed from the autoclave and separated into two fractions. One fraction is analyzed by means of wet-chemical analysis, said analysis disclosing the treatment product to be tri-n-octyl aluminum, di-n-octyl aluminum and n-octyl aluminum hydride.

The second fraction of the recovered treatment product is charged to a second rotating autoclave containing 0.3 grams of bis-(tributyl phosphine) nickel chloride, said autoclave being equipped with heating, carbon monoxide and hydrogen entry devices. The autoclave is heated to a temperature of 160°C and maintained at a pressure of 500 psi of carbon monoxide and 500 psi of hydrogen for a period of time comprising 24 hours. After the 24 hour period of time the heat is terminated thereby allowing the autoclave to return to room temperature and the autoclave vented thereby allowing it to return to ambient pressure, at which point in time the reaction product is removed from the autoclave, separated from the catalyst and analyzed by means of gas-liquid chromatography. The gas-liquid chromatography analysis will disclose the product to be linear aldehydes and alcohols having a smaller quantity of branched isomers than normally expected in a hydroformylation reaction product.

EXAMPLE II

In this example 13.0 grams of a liquified mixture comprising butene-2, pentene-2, hexene-3, butene-1, pentene-1 and hexene-1, 0.4 grams of diisopropyl aluminum hydride and 1.0 grams of aluminum are charged to a rotating autoclave equipped with heating and hydrogen entry devices. The autoclave is heated to a temperature of 50°C and charged with hydrogen gas to effect the pressure of 4000 psi, said physical conditions of pressure and temperature maintained at constant values for a period of time comprising 5 hours. At the end of the 5 hour period of time the autoclave is vented thereby allowing it to return to ambient pressure and the heat terminated thereby allowing it to return to room temperature at which point in time the treatment product is removed from the autoclave and separated into two fractions. One fraction is analyzed by means of wet-chemical analysis, said analysis disclosing the treatment product to be tri, di and mono alkyl aluminum compounds containing between 4 and 6 carbon atoms.

The second fraction of the recovered treatment product is charged to a second rotating autoclave containing 0.5 grams of triphenyl phosphine rhodium chloride, said autoclave being equipped with heating, carbon monoxide and hydrogen entry devises. The autoclave is heated to a temperature of 200°C and maintained at a pressure of 1000 psi of carbon monoxide and 1000 psi of hydrogen for a period of time comprising 18 hours. After the 18 hour period of time the heat is terminated thereby allowing the autoclave to return to room temperature and the autoclave vented thereby allowing it to return to ambient pressure, at which point in time the reaction product is removed from the autoclave, separated from the catalyst and analyzed by means of gas-liquid chromatography. The gas-liquid chromatography analysis will disclose the product to comprise linear aldehydes and alcohols having carbon numbers in the range of about 5 to about 7, said products will have a smaller quantity of branched isomers than normally expected in a hydroformylation reaction product.

EXAMPLE III

In this example a continuous process for the production of linear aldehydes and alcohols is maintained as hereinafter set forth. A charge stock comprising a mixture of undecene-5, dodecene-4, tridecene-6, tetradecene-4, undecene-1, dodecene-1, tridecene-1 and tetradecene-1 is charged to a treatment zone containing triethyl aluminum, aluminum metal and a hydrogen gas entry device, said zone being maintained at a temperature of 200°C and a pressure of 1500 psi as afforded by the introduction of hydrogen gas. The residence time of the unsaturated compounds, aluminum-containing compound and aluminum metal in the treatment zone is maintained at 30 minutes, at which point in time the treatment product is recovered from the treatment zone.

The recovered treatment product is subsequently charged to a reactor zone containing tributyl phosphine cobalt chloride, carbon monoxide and hydrogen gas entry ports. The reactor zone is maintained at a temperature of 250°C and a pressure of 3000 psi as a result of the introduction of 1500 psi of hydrogen and 1500 psi of carbon monoxide for a period of time so as to afford a residence time of 1.5 hours. At the end of the 1.5 hour residence time the product is withdrawn as the reactor effluent and subjected to analysis by gas-liquid chromatography instrumentation, said analysis will disclose the reaction product to be linear aldehydes and alcohols having a smaller quantity of branched isomers than is normally expected in a hydroformylation reaction product.

The above set forth continuous production of linear aldehydes and alcohols is repeated by first substituting octene-3 as the unsaturated compound and bis-cyclooctadienyl nickel as the reaction zone catalyst and second by substituting octene-3 as the unsaturated compound, tributyl ruthenium chloride as the reaction zone catalyst and diisopropyl aluminum hydride as the treating agent. In both cases the reaction product analysis will disclose the reaction product to be linear aldehydes and alcohols having a smaller quantity of branched isomers than is normally expected in a hydroformylation reaction product.

I claim as my invention:

1. A process for the preparation of a linear primary alkanol or alkanal which comprises reacting a mono-olefinic hydrocarbon possessing from 3 to 21 carbon atoms in a hydrogen atmosphere with aluminum metal and a compound selected from the group consisting of triethyl aluminum and diisopropyl aluminum hydride at a temperature of from about 50°C to about 200°C and a pressure of from about 14 to 4000 psi to form a tri-n-alkyl aluminum compound, reacting said tri-n-alkyl aluminum compound with carbon monoxide and hydrogen at a temperature of from about 25°C to about 400°C and a pressure of from about 14 to about 4000 psi in the presence of a hydroformylation catalyst selected from the group consisting of bis-(tributyl phosphine) nickel chloride and triphenyl phosphine rhodium chloride and recovering the resultant linear primary alkanol or alkanal.

2. The process of claim 1 further characterized in that the resultant product is a linear aldehyde.

3. The process of claim 1 further characterized in that the resultant product is a linear alcohol.

4. The process of claim 1 further characterized in that the resultant product is a mixture of a linear aldehyde and a linear alcohol.

5. The process of claim 1 further characterized in that the unsaturated compounds comprise both internal and terminal olefins.

6. The process of claim 5 further characterized in that the internal olefins are butene-2, pentene-2 and hexene-3 and the terminal olefins are butene-1, pentene-1 and hexene-1.

7. The process of claim 5 further characterized in that the internal olefins are undecene-5, dodecene-4, tridecene-6 and tetradecene-4 and the terminal olefins are undecene-1, tridecene-1 and tetradecene-1.

8. The process of claim 1 further characterized in that the unsaturated compound is octene-3.

* * * * *